United States Patent [19]
Houser et al.

[11] Patent Number: 5,957,980
[45] Date of Patent: Sep. 28, 1999

[54] REINFORCEMENT ASSEMBLY FOR LAMINATED STRUCTURES

[75] Inventors: Guy Houser; Stewart L. Atkinson, both of Bainbridge Island, Wash.

[73] Assignee: Model & Instrument Development Corporation, Poulsbo, Wash.

[21] Appl. No.: 08/926,172

[22] Filed: Sep. 9, 1997

[51] Int. Cl.⁶ .................................................. A61F 2/80
[52] U.S. Cl. ................ 623/36; 623/33; 264/222
[58] Field of Search .............. 623/33–37; 602/62, 602/63; 264/222, DIG. 30; 425/2

[56] References Cited

U.S. PATENT DOCUMENTS

| | | | |
|---|---|---|---|
| 5,139,523 | 8/1992 | Paton et al. | 623/37 |
| 5,263,990 | 11/1993 | Handal | 623/57 |
| 5,718,925 | 2/1998 | Kristinsson et al. | 425/2 |

FOREIGN PATENT DOCUMENTS

| | | | |
|---|---|---|---|
| 2 104 386 | 3/1983 | United Kingdom | 623/33 |

*Primary Examiner*—David H. Willse
*Attorney, Agent, or Firm*—Seed and Berry, LLP

[57] ABSTRACT

A reinforcement assembly to reinforce a selected site on a body, and methods of making and using such a universal reinforcement assembly. Several embodiments of reinforcement assemblies in accordance with the principles of the invention are well suited to support or reinforce laminated structures. In one embodiment, the reinforcement assembly has a reinforcement member configured to be attached to the selected site on the body and a universal attachment medium separately bonded to the reinforcement member. The reinforcement member may be a plate composed of a molding compound, a high density polymer, or another suitable high-strength material. The universal attachment medium, more specifically, may have a first section bonded to the reinforcement member and a second section extending from the reinforcement member to cover an area of the body substantially surrounding the selected site. The attachment medium may be composed of a self-conforming material that inherently conforms to the shape of the body to define an anchor stratum of the laminated structure having a shape corresponding to the area of the body substantially surrounding the selected site.

30 Claims, 6 Drawing Sheets

REINFORCEMENT ASSEMBLY FOR LAMINATED STRUCTURES

TECHNICAL FIELD

The present invention generally relates to reinforcing laminated structures. More specifically, an embodiment of the present invention relates to a universal reinforcement assembly for reinforcing selected sites of prosthetic limbs.

BACKGROUND OF THE INVENTION

Prosthetic devices, such as prosthetic limbs, are typically lightweight components that replace damaged or missing body parts of a particular patient. Many prosthetic devices are subject to significant forces applied via complex, variable motions of the surrounding body parts. Selected sites on prosthetic devices are accordingly reinforced to withstand particularly large loads. However, reinforcing selected sites on leg sockets and other devices without increasing the weight and cost of the devices is difficult.

FIG. 1A is an exploded isometric view of a conventional leg socket 10 that may be attached to a leg stump S of a particular patient P. The socket 10 typically has a lightweight liner 12 composed of a thermoplastic or fiberglass sheet that is shaped to fit the contour of the leg stump S. The leg socket 10 may also have a connector assembly 20 having a base 22, a plurality of fingers or legs 24 projecting from the base 22, and an inverted pyramid 26 projecting from the base 22. The connector assembly 20 is generally a rigid metal component attached to the distal end of the liner 12, and the inverted pyramid 26 is configured to engage a mating adapter on a pylon (not shown). Other connector assembly structures may, of course, be used, and an outer shell (not shown) is typically laminated over the liner 12 and the legs 24.

FIG. 1B is a partial isometric view of the connector assembly 20 attached to the liner 12 of the leg socket 10. To attach the connector assembly 20 to the liner 12, a prosthetist manually deforms the legs 24 of the connector assembly 20 to roughly fit the liner 12. The prosthetist, for example, generally bends the legs 24 downwardly from the base 22 and hammers selected points along each leg 24 to roughly fit each leg 24 to the particular area on the liner 12. After the legs 24 are deformed to roughly fit the particular geometry of the liner 12, the legs 24 are secured to the liner 12 with a plurality of fasteners 28. The prosthetist then laminates an outer sheet of fiberglass (not shown) to the legs 24 and the liner 12 with a resin binder to form the leg socket 10.

Reinforcing the leg socket 10 with the connector assembly 20 generally increases the costs and reduces the performance of the prosthetic limb. For example, attaching the connector assembly 20 to the liner 12 is extremely time-consuming because the prosthetist manually deforms each of the metal legs 24 with a hammer to fit the geometry of the liner 12. Additionally, attaching the connector assembly 20 to the liner 12 is also imprecise because the legs 24 may not accurately conform to depressions 18 (shown exaggerated) or other topographical features on the surface 16 of the liner 12. Many leg sockets 10 with metal connector assemblies 20 are thus subject to significant point loading at various locations between the legs 24 and the liner 12 or outer fiberglass layer (not shown). As a result, the thickness of the liner 12 and the subsequent outer fiberglass layer are increased to sustain the point loading caused by the connector assembly 20. It will be appreciated that the significant time requirements and additional materials increase the weight and cost of the leg socket 10.

FIG. 2A is a partial isometric view of another conventional leg socket 10a with an liner 12 and a connector assembly 20a connected to the liner 12. The connector assembly 20a has a plurality of cables 24a extending from the base 22. In operation, the prosthetist lays the cables 24a over the surface 16 of the liner 12 and laminates an outer sheet of fiberglass (not shown) over the liner 12 and the legs 24a. The connector assembly 20a does not require as much time to install as the connector assembly 20 shown in FIG. 1B because the prosthetist does not need to hammer each of the cables 24a to fit the geometry of the liner 12. The connector assembly 20a, however, may produce significant point loading along the cables 24a because each cable 24a transmits forces to discrete, isolated areas of the liner 12 and the outer fiberglass layer. Moreover, most of the force applied to the connector assembly 20a acts against the resin and the outer fiberglass layer because the cables 24a are not fastened to the liner 12 and the cables 24a act separately from the resin. Therefore, it is also necessary to make the socket 10a with substantially thick walls in the region of the connector 20a to withstand the forces generated in typical installations.

FIG. 2B is a partial isometric view of yet another conventional leg socket 10b with another connector assembly 20b attached to the liner 12. The connector assembly 20b has a base 22b with first and second slots 23 and 25 extending perpendicular to one another across the top of the base 22b. A first strip $24b_1$ positioned in the first slot 23 projects from a first set of opposing sides of the base 22b, and a second strip $24b_2$ positioned in the second slot 25 projects from a second set of opposing sides of the base 22b. The prosthetist attaches the connector assembly 20b to the liner 12 by positioning the strips $24b_1$ and $24b_2$ in the slots 23 and 25, and then laminating an outer sheet of fiberglass over the base 22b, the strips $24b_1$ and $24b_2$, and the liner 12. A separate pylon connector 30 with a pyramid 32 is then attached to the base 22b. The connector assembly 20b also reduces the installation time compared to the metal connector assembly 20 because the prosthetist can more easily deform the strips $24b_1$ and $24b_2$ to conform to the geometry of the liner 12. However, as with the connector assembly 20a shown in FIG. 2A, the connector assembly 20b also produces point loading in the resin binder, the fiberglass outer sheet, and the liner 12. As a result, the leg socket 10b also has thick walls in the region of the connector assembly 20b.

SUMMARY OF THE INVENTION

The present invention is a universal reinforcement assembly to reinforce a selected site on a body. Several embodiments of reinforcement assemblies are well suited to support or reinforce laminated structures. In one embodiment, the reinforcement assembly has a reinforcement member configured to be attached to the selected site on the body and a universal attachment medium separately bonded to the reinforcement member. The reinforcement member may be a plate composed of a molding compound, a high density polymer, or another suitable high-strength material. The universal attachment medium, more specifically, may have a first section bonded to the reinforcement member and a second section extending from the reinforcement member to cover an area of the body substantially surrounding the selected site. The attachment medium may be composed of a self-conforming material that inherently conforms to the shape of the body to define an anchor stratum of the laminated structure having a shape corresponding to the area of the body substantially surrounding the selected site.

Several embodiments of universal reinforcement assemblies are particularly well suited for medical device applications. In one embodiment, for example, a universal reinforcement assembly for a prosthetic limb has a reinforcement member configured to be attached to a liner of the prosthetic limb at a selected site subject to force loading. A first section of a universal attachment medium is bonded to the reinforcement member and a second section extends from the reinforcement member to cover a force distribution area of the liner substantially surrounding the selected site. More specifically, the first section of the attachment medium may be fused to the reinforcement member to integrally bond the attachment medium to the reinforcement member at an integral joint. The second section of the attachment medium may be composed of a material that inherently conforms to a defined shape of the liner corresponding to a particular limb of a specific patient when the reinforcement member is positioned at the selected site. For example, the attachment medium may be a lax web that lays slack on the liner and follows the topography of the liner prior to laminating an outer layer over the attachment medium. Suitable types of webs are fiberglass sheets, woven or braided meshes of carbon graphite strands, or other highly flexible materials that conform to the shape of an object without significant manipulation.

In one particular embodiment of a universal reinforcement assembly used on a leg socket, the reinforcement member may have first and second plates of a molding compound, and the attachment medium may be a tubular woven mesh of carbon graphite strands. The first and second plates of molding compound are positioned on opposite sides of an end portion of the tubular mesh that projects radially inwardly toward a center line of the tube. The first and second plates of molding compound are fused with the end section of the attachment medium using a curing process to form an integral joint connecting the attachment medium to the reinforcement member. The curing process also melds the first and second plates together to form a unitary block of rigid, high-strength molding compound.

After the first section of the attachment medium is fused with the reinforcement member, the universal reinforcement assembly may be attached to the liner. More particularly, a prosthetist may place the reinforcement member at the selected site on the liner and laminate the attachment medium to the liner with an outer fiberglass sheet and a resin binder. Because the attachment medium is self-conforming, it inherently conforms to the force distribution area on the liner as the reinforcement member is placed at the selected site. Therefore, an embodiment of the attachment medium is ready to be laminated to the liner without significant mechanical manipulation and it distributes the forces applied to the reinforcement member over a large surface area to reduce point loading in the laminated structure.

DETAILED DESCRIPTION OF THE INVENTION

The present invention is an apparatus and method for reinforcing a portion of a laminated structure or other type of body. Many specific details of certain embodiments of the invention are set forth in the following description and in FIGS. 3–5B to provide a thorough understanding of such embodiments of the invention. One skilled in the art, however, will understand that the invention may have additional embodiments and may be practiced without several of the details described in the following description.

Figure 1A:
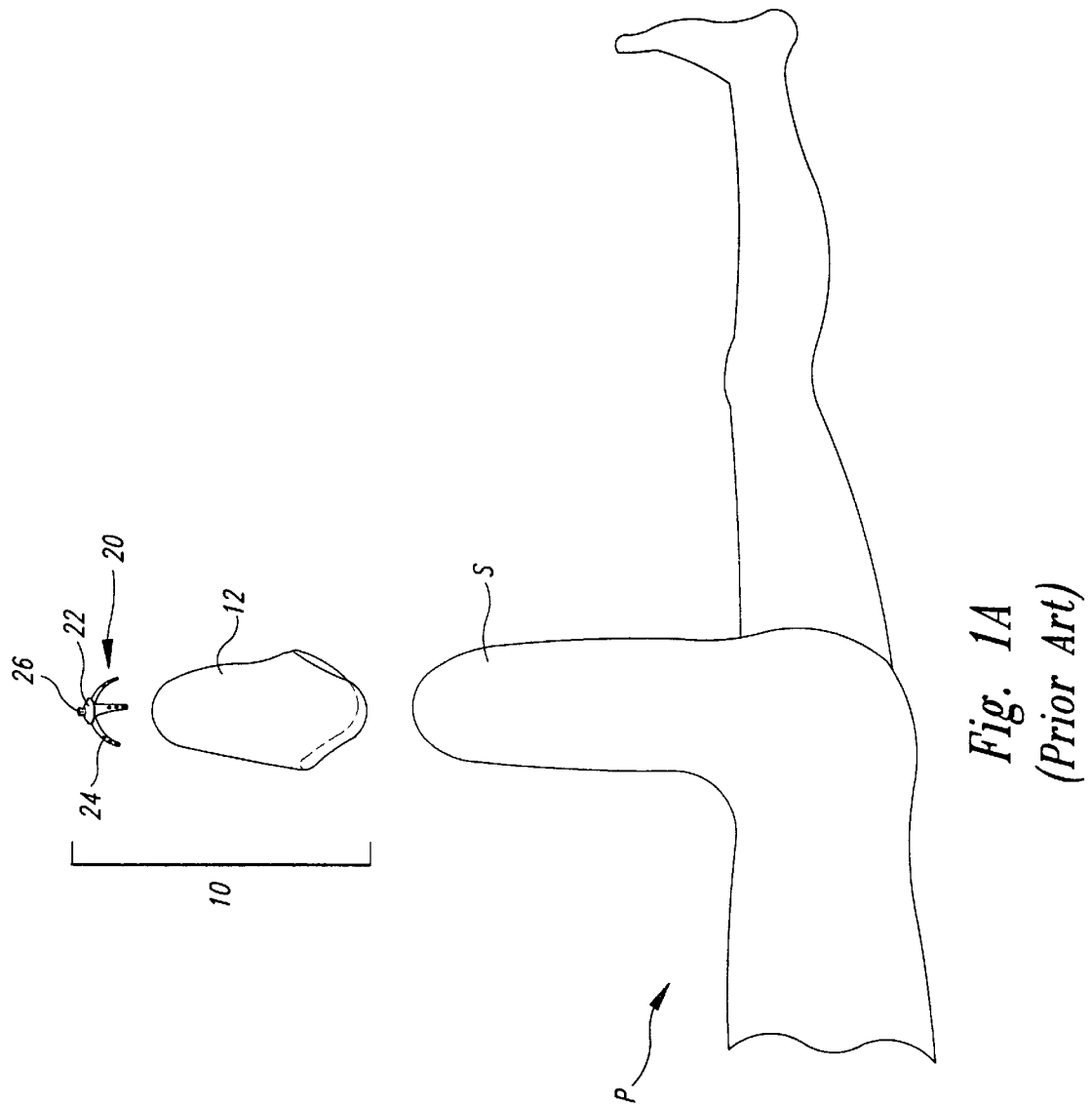
FIG. 1A is a schematic isometric view of a leg socket for a particular patient in accordance with the prior art.
Figure 2A:
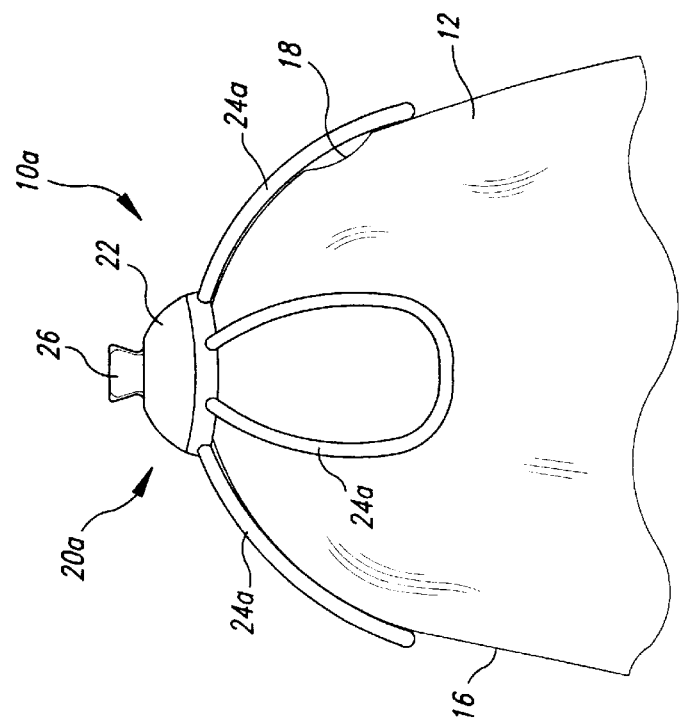
FIG. 2A is a partial isometric view of another leg socket in accordance with the prior art.
Figure 1B:
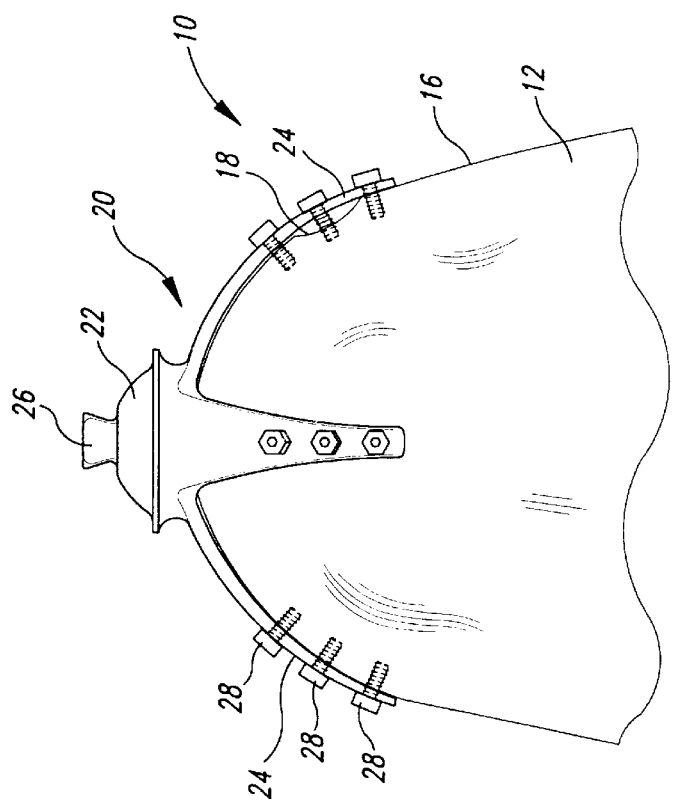
FIG. 1B is a partial isometric view of the leg socket of FIG. 1A.
Figure 2B:
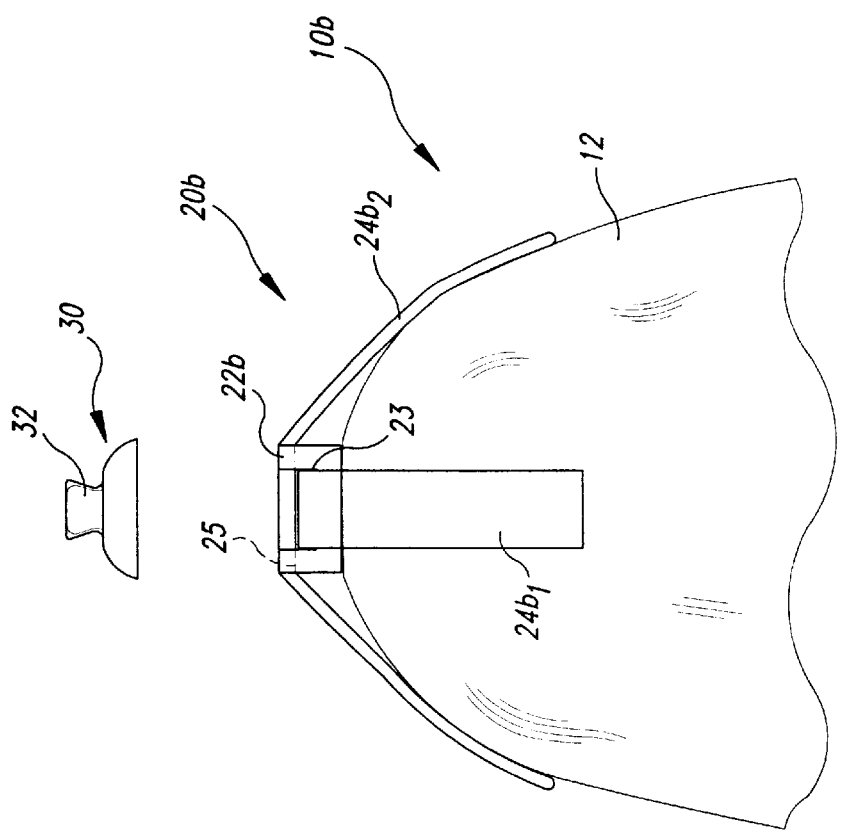
FIG. 2B is a partial isometric view of still another leg socket in accordance with the prior art.
Figure 3:
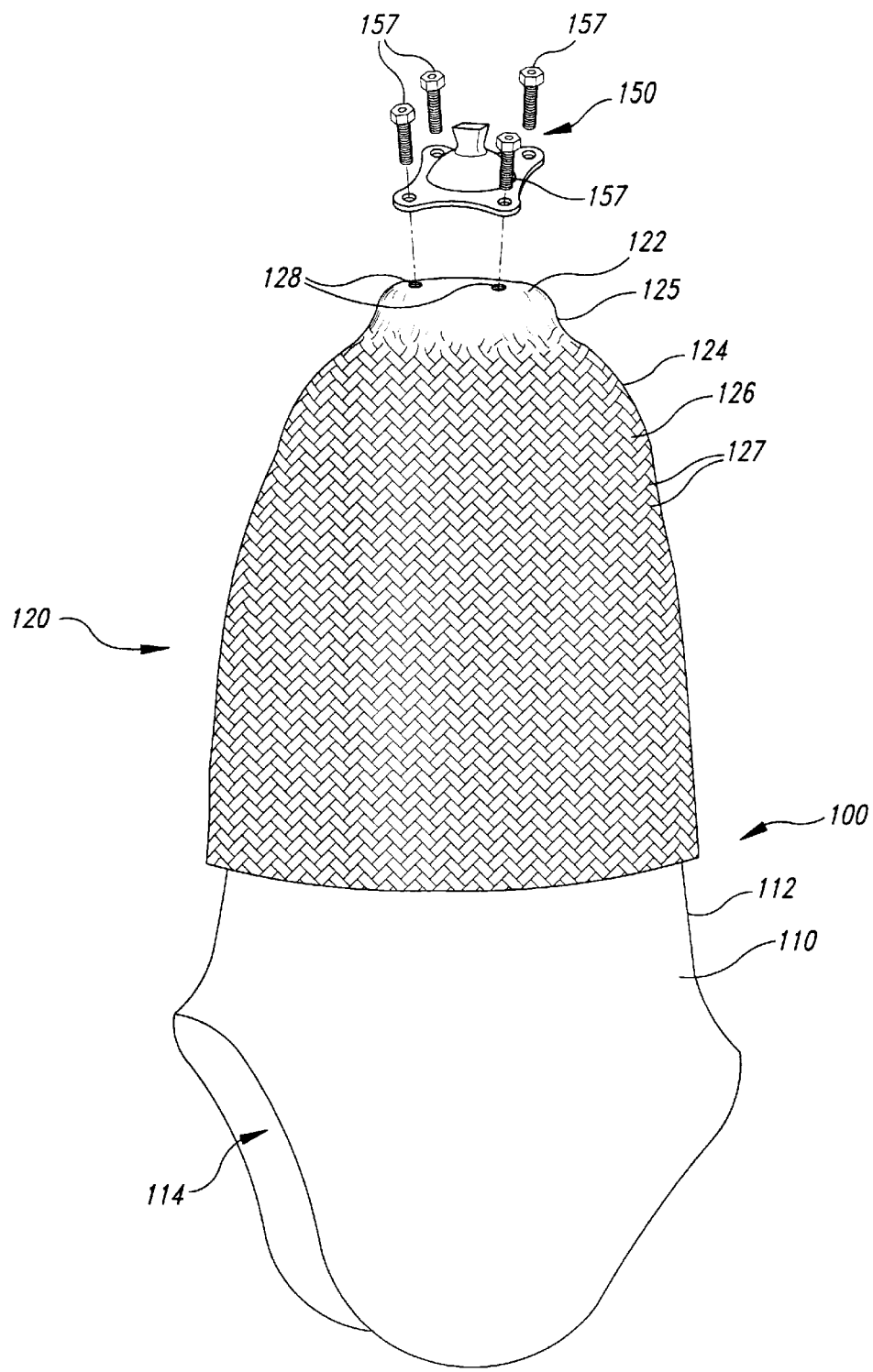
FIG. 3 is an exploded isometric view of an liner of a leg socket with a universal reinforcement assembly in accordance with one embodiment of the invention.

FIG. 3 is an exploded isometric view of a portion of a leg socket 100 with an embodiment of a reinforcement assembly 120 for reinforcing a distal end of the leg socket 100. The leg socket 100 and the reinforcement assembly 120 illustrate only one application and one embodiment of reinforcement assemblies in accordance with the invention. In this particular embodiment, the reinforcement assembly 120 covers a portion of a shell or liner 110 that has an outer surface 112 and a cavity 114. The liner 110 is shaped so that the leg stump (not shown) of a particular patient comfortably fits in the cavity 114. The liner 110, therefore, is typically custom made from a mold corresponding to the leg stump of the particular patient.

The reinforcement assembly 120 shown in FIG. 3 has a reinforcement member 122 configured to be positioned at a selected site on the liner 110 where additional strength is required. The reinforcement member 122 may be a rigid, high-strength plate or bar composed of a sheet molding compound (SMC), a bulk molding compound (BMC), high-density acetyl polymers (e.g, Dehrin® manufactured by E. I. Dupont de Nemours of Wilmington, Del.), or other suitable strength materials. The size and shape of the reinforcement member 122 is a function of the shape of the body and the forces exerted on the reinforcement member 122. In the embodiment of the leg socket 100 shown in FIG. 3, the reinforcement member 122 is generally a circle or square block with a thickness between 0.25 and 0.75 inches to provide an adequate base for supporting a pylon connector 150. A number of threaded sleeves 128 are preferably inserted into holes of the reinforcement member 122 to receive fasteners 157 that attach the pylon connector 150 to the reinforcement member 122. It will be appreciated, however, that the reinforcement member 122 is not limited to a thickness of 0.25–0.75 inches, and that many other sizes and shapes of reinforcement members may be used.

The reinforcement assembly 120 shown in FIG. 3 also has an attachment medium 124 with a first section 125 bonded to the reinforcement member 122 and a second section 126 extending from the reinforcement member 122. The first section 125 of the attachment medium 124 may be fused to the reinforcement member 122 to form an integral joint connecting the attachment medium 124 to the reinforcement member 122. In another embodiment, the first section 125 may be bonded to the reinforcement member 122 with an adhesive to form a cemented joint. The particular bond between the first section 125 of the attachment medium 124 and the reinforcement member 122 depends upon the particular application of the reinforcement assembly 120. When the reinforcement assembly 120 is used in a leg prosthesis, the first section 125 of the attachment medium 124 is fused with the reinforcement member 122 by cocuring the attachment medium 124 and the reinforcement member 122 under high temperature and pressure conditions.

The second section 126 of the attachment medium 124 extends from the reinforcement member 122 to preferably cover a force distribution area of the liner 110. The particular force distribution area is a function of the type of body to which the reinforcement assembly 120 is to be attached and the forces applied to the reinforcement member 122. In the embodiment of the leg socket 100 shown in FIG. 3, the force distribution area surrounds the selected site at the distal end of the liner 10. As such, the second portion 126 of the attachment medium 124 preferably is a contiguous web that extends from the full perimeter of the reinforcement member 122 to an intermediate line around the liner 110. It will be appreciated, however, that the attachment medium 124 does not need to cover all of the surface area surrounding the selected site, and that the second section 126 may have other configurations.

The attachment medium 124, or at least the second section 126 of the attachment medium 124, preferably inherently conforms to the topography of the surface 112 of the liner 110. More specifically, the attachment medium 124 may be a lax web, braid or mesh that: (1) bonds well with the reinforcement member 122; (2) self-conforms to the body to which the reinforcement assembly 120 is attached; (3) bonds well with the body; and (4) has good stress/strain characteristics to withstand and distribute the forces exerted on the reinforcement member 122. In one particular embodiment, the attachment medium 124 is a woven mesh of carbon graphite strands 127 that lays against the surface 112 of the liner 110. However, other suitable materials from which the attachment medium 124 may be composed include fiberglass or any other web that generally conforms to a topography of the body by simply smoothing the web over the surface.

Figure 4:
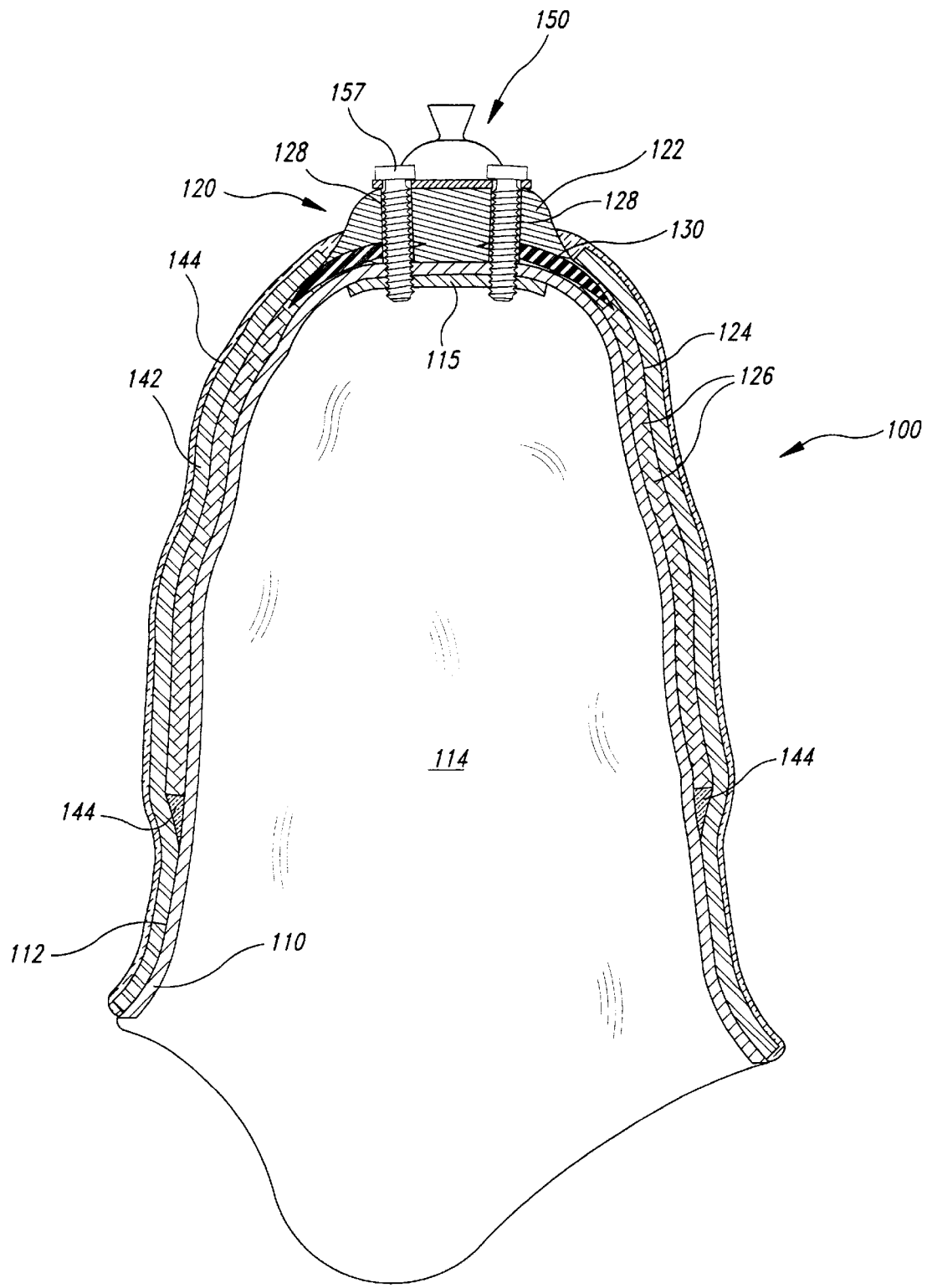
FIG. 4 is a cross-sectional view of the universal reinforcement assembly of FIG. 3 shown laminated to the liner to form a prosthetic leg socket in accordance with one embodiment of the invention.

FIG. 4 is a cross-sectional view of a complete leg socket 100 in which the reinforcement assembly 120 is part of a laminated structure. In this embodiment, the liner 110, the reinforcement assembly 120, and an outer fiberglass sheet 142 are laminated together with a resin binder 144 to form a laminated structure. The resin binder 144 is preferably spread over the liner 110, the attachment medium 124 and the outer fiberglass sheet 142 to securely bond these items together into a high-strength, low-weight structure. As best seen in FIG. 4, the first section 125 of the attachment medium 124 is fused to the reinforcement member 122 at an integral joint 130, and the second section 126 of the attachment medium 124 conforms to the topography of the outer surface 112 of the liner 110. The second section 126 of the attachment medium 124 accordingly defines an anchor stratum in the laminated structure having a size and shape corresponding to the force distribution area on the liner 110. Additionally, the fasteners 157 may be threadably engaged with the sleeves 128 in the reinforcement member 122 and a back-plate 115 in the cavity 114 to attach the pylon connector 150 and further secure the reinforcement member 122 to the assembly.

The embodiment of the reinforcement assembly 120 illustrated in FIGS. 3 and 4 provides several advantages compared to conventional connector assemblies attached to conventional leg sockets. For example, compared to the conventional connector assemblies described above in FIGS. 1A–2B, the reinforcement assembly 120 significantly reduces the time required to construct the leg socket 100 because the attachment medium 124 inherently conforms to the shape of the liner 110. As a result, the prosthetist is not required to machine or hammer the attachment medium 124 to fit the particular geometry of the liner 110. A prosthetist may accordingly manufacture more leg sockets in a given period of time to significantly increase the production of prosthetic devices.

Another advantage of the embodiment of the reinforcement assembly 120 is that it distributes and absorbs forces to reduce point loading in the laminated structure. Unlike conventional connector assemblies, an embodiment of the attachment medium 124 conforms to the contour of the liner 110 and covers a substantial surface area of the liner 110 adjacent to the selected site to which the reinforcement member 122 is positioned. The forces exerted on the reinforcement member 122 are accordingly distributed over a large, conformal medium that reduces force concentrations at particular points in the laminated structure. Additionally, the fibers in the second section 126 of the attachment medium 124 and the resin 144 proximate to the fibers absorb some of the forces to reduce the magnitude of force transferred to the liner 110 and the fiberglass layer 142. The thickness of the laminated structure in the leg socket 100, therefore, is substantially less than that of conventional leg sockets. Thus, the leg socket 100 is generally lighter and more comfortable than conventional leg sockets.

Figure 5A:
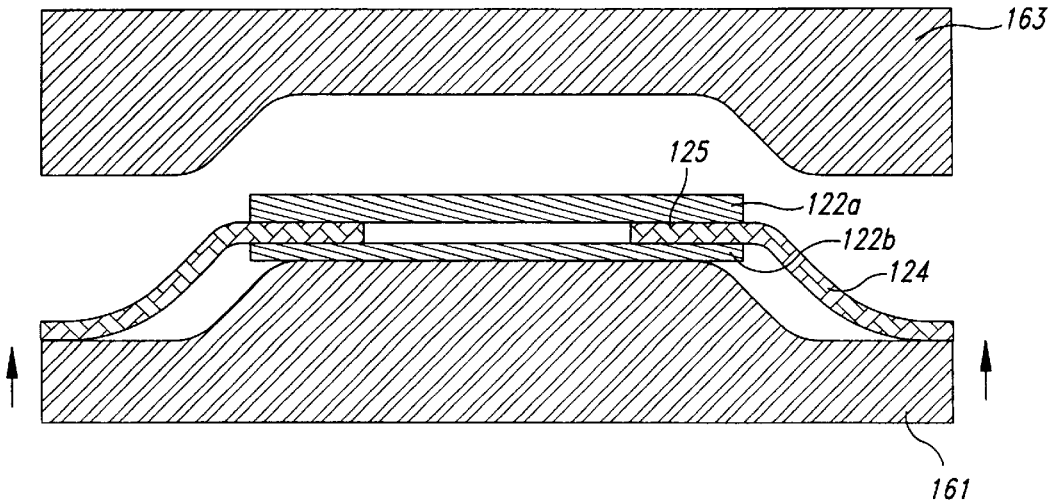
FIG. 5A is a schematic partial cross-sectional view of one stage in a method for making a universal reinforcement assembly in accordance with one embodiment of the invention.
Figure 5B:
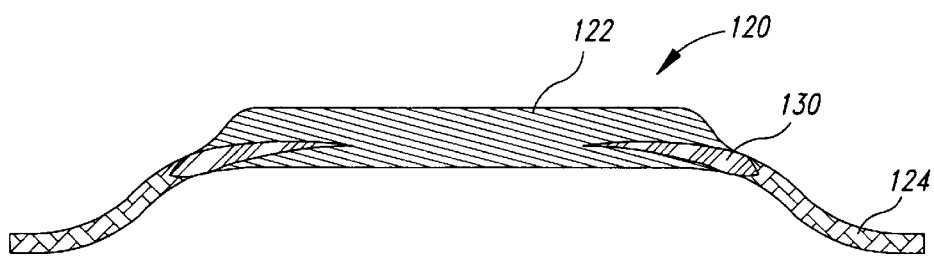
FIG. 5B is a schematic partial cross-sectional view of the universal reinforcement assembly of FIG. 5A at a subsequent stage in the method of fabricating a universal reinforcement assembly.

FIG. 5A is a schematic cross-sectional view that illustrates one stage in a method for making an embodiment of the reinforcement assembly 120. In this embodiment, first and second plates 122a and 122b of a molding compound are positioned on opposite sides of the first section 125 of the attachment medium 124. The first and second plates 122a and 122b are preferably partially cured or "B-stage" SMC or BMC that is not fully hardened prior to curing. A pair of male and female tools 161 and 163 configured to shape the first and second plates 122a and 122b in the desired shape of the reinforcement member 122 are then pressed together in a heated environment to meld the first and second plates 122a and 122b into a unitary reinforcement member 122 of cured molding compound. The high-pressure and temperature curing process also fuses the first and second plates 122a and 122b with the first section 125 of the attachment medium 124 to form an integral joint 130 around the perimeter of the reinforcement assembly 122 (FIG. 5B). In a specific application of the process in which the first and second plates are composed of SMC and the attachment medium 124 is a carbon and graphite mesh, the male and female tools 161 and 163 are pressed together at 1000 psi under a temperature of 250° F. for five minutes.

From the foregoing it will be appreciated that, although specific embodiments of the invention have been described herein for purposes of illustration, various modifications may be made without deviating from the spirit and scope of the invention. For example, the reinforcement assembly may have a plurality of separate reinforcement members bonded to a single attachment medium. Additionally, the reinforcement assemblies may have reinforcement members composed of a single plate of molding compound that is fused to the attachment medium under suitable pressure, temperature and time conditions. Accordingly, the invention is not limited except as by the appended claims.

We claim:

1. A reinforcement assembly for prosthetic limbs, comprising:

a reinforcement member configured to be attached to a selected site on a liner of a prosthetic limb, the reinforcement member having a high strength and the liner having a distinct shape corresponding to a specific patient; and an attachment medium having a first section bonded to the reinforcement member and a second section extending from the reinforcement member, the second section of the attachment medium being a conformal material that forms to the distinct shape of the liner over an area at least substantially surrounding the selected site to define an anchor stratum over the area at least substantially surrounding the selected site, wherein the attachment medium comprises a web and the bond between the first section of the attachment medium and the reinforcement member comprises a fused section in which a portion of the attachment medium and a portion of the reinforcement member form an integral joint.

2. The reinforcement assembly of claim 1 wherein the attachment medium comprises a lax web adapted to lay slack on the liner prior to being laminated with the liner.

3. The reinforcement assembly of claim 2 wherein the web comprises a fiberglass sheet.

4. The reinforcement assembly of claim 2 wherein the web comprises a woven mesh.

5. The reinforcement assembly of claim 4 wherein the woven mesh comprises a contiguous braid of carbon graphite strands.

6. The reinforcement assembly of claim 1 wherein the web comprises a woven mesh of carbon graphite strands and the reinforcement member comprises a plate of molding compound, the molding compound being partially cured prior to being fused with the first section of the attachment medium, and wherein the integral joint is formed by pressing the attachment medium and the reinforcement member together at an elevated temperature.

7. The reinforcement assembly of claim 1 wherein the web comprises a woven mesh of carbon graphite strands and the reinforcement member comprises a first plate of molding compound positioned on one side of the woven mesh and a second plate of molding compound positioned on another side of the woven mesh juxtaposed to the first plate of molding compound, the first and second plates of molding compound being partially cured prior to being fused with the first section of the attachment medium, and wherein the integral joint is formed by pressing the first and second plates of molding compound against the sides of the attachment medium at an elevated temperature.

8. The reinforcement assembly of claim 1 wherein:

the attachment medium comprises a tubular woven mesh of carbon graphite strands;

the reinforcement member comprises a plate of molding compound; and the bond between the first section of the attachment medium and the reinforcement member comprises a fused section in which an end portion of the tubular mesh and a portion of the reinforcement member are combined into an integral joint around a perimeter of the reinforcement member.

9. The reinforcement assembly of claim 8 wherein:

the first section of the attachment medium comprises an end portion of the tubular mesh projecting radially inwardly toward a centerline of the tubular mesh; and the reinforcement member comprises a first plate of molding compound positioned on one side of the end portion and a second plate of molding compound positioned on another side of the end portion juxtaposed to the first plate of molding compound, the first and second plates of molding compound being partially cured prior to being fused with the end portion of the tubular mesh, and wherein the integral joint is formed by pressing the first and second plates of molding compound against the end portion of the tubular mesh at an elevated temperature.

10. A reinforcement assembly for prosthetic limbs, comprising:

a reinforcement member configured to be attached to a selected site on a liner of a laminated prosthetic limb, the reinforcement member having a high strength and the liner having a custom shape corresponding to a particular patient; and a universal attachment medium extending from the reinforcement member to cover a force distribution area of the liner substantially surrounding the selected site, the attachment medium having a first section fused to the reinforcement member to form an integral joint connecting the attachment medium to the reinforcement member, and the attachment medium having a second section inherently conforming to the custom shape of the liner at the force distribution area when the reinforcement member is positioned at the selected site.

11. The reinforcement assembly of claim 10 wherein the attachment medium comprises a contiguous woven mesh of carbon graphite strands.

12. The reinforcement assembly of claim 11 wherein the reinforcement member comprises a plate of molding compound, the molding compound being partially cured prior to being fused with the first section of the graphite mesh, and wherein the integral joint is formed by pressing the plate of molding compound and the graphite mesh together at an elevated temperature.

13. The reinforcement assembly of claim 11 wherein the reinforcement member comprises a first plate of molding compound positioned on one side of the graphite mesh and a second plate of molding compound positioned on another side of the graphite mesh juxtaposed to the first plate of molding compound, the first and second plates of molding compound being partially cured prior to being fused with a section of the graphite mesh, and wherein the integral joint is formed by pressing the first and second plates of molding compound against the sides of the graphite mesh at an elevated temperature.

14. A reinforcement assembly in a laminated structure of a prosthetic device, comprising:

a reinforcement member configured to be attached to a selected site on a body subject to force loading, the reinforcement member having a high strength; and a universal attachment medium separately bonded to the reinforcement member to extend from the reinforcement member over an area of the body substantially surrounding the selected site, the attachment medium being self-conforming to the body to define an anchor stratum in the laminated structure having a shape corresponding to the area of the body substantially surrounding the selected site, wherein the attachment medium comprises a lax web configured to lay slack on the body prior to lamination and the bond between of the attachment medium and the reinforcement member comprises a fused section in which a portion of the attachment medium and a portion of the reinforcement member form an integral joint.

15. The reinforcement assembly of claim 14 wherein the lax web is configured to generally conform to a topography of the body when the reinforcement member is mounted to the selected site.

16. The reinforcement assembly of claim 15 wherein the web comprises a fiberglass sheet.

17. The reinforcement assembly of claim 15 wherein the web comprises a woven mesh.

18. The reinforcement assembly of claim 17 wherein the woven mesh comprises a contiguous braid of carbon graphite strands.

19. The reinforcement assembly of claim 14 wherein the web comprises a woven mesh of carbon graphite strands and the reinforcement member comprises a plate of molding compound, the molding compound being partially cured prior to being fused with the attachment medium, and wherein the integral joint is formed by heating and pressing the attachment medium and the reinforcement member together.

20. The reinforcement assembly of claim 14 wherein the web comprises a woven mesh of carbon graphite strands and the reinforcement member comprises a first plate of molding compound positioned on one side of the woven mesh and a second plate of molding compound positioned on another side of the woven mesh juxtaposed to the first plate of molding compound, the first and second plates of molding compound being partially cured prior to being fused with the woven mesh, and wherein the integral joint is formed by pressing the first and second plates of molding compound against the sides of the woven mesh at an elevated temperature.

21. The reinforcement assembly of claim 15 wherein:
the attachment medium comprises a tubular woven mesh of carbon graphite strands;
the reinforcement member comprises a plate of molding compound; and
the bond between of the attachment medium and the reinforcement member comprises a fused section in which an end portion of the tubular mesh and a portion of the reinforcement member are combined into an integral joint around a perimeter of the reinforcement member.

22. A reinforcement assembly for use in a laminated structure of a prosthetic device formed on a body, comprising:
a reinforcement member configured to be attached to a selected site on the body subject to force loading, the reinforcement member having a high strength and the body having a defined shape; and
a universal attachment medium having a first section fused to the reinforcement member to integrally join the attachment medium to the reinforcement member and a second section extending from the reinforcement member, the second section of the attachment medium being a lax material that inherently conforms to the area of the body proximate to the selected site to define an anchor stratum in the laminated structure having a shape corresponding to the area of the body proximate to the selected site.

23. The reinforcement assembly of claim 22 wherein the attachment medium comprises a contiguous web.

24. The reinforcement assembly of claim 23 wherein the web comprises a fiberglass sheet.

25. The reinforcement assembly of claim 23 wherein the web comprises a woven mesh of carbon graphite strands.

26. The reinforcement assembly of claim 25 wherein the bond between the first section of the attachment medium and the reinforcement member comprises a fused section in which a portion of the attachment medium and a portion of the reinforcement member form an integral joint.

27. The universal reinforcement assembly of claim 26 wherein the reinforcement member comprises a plate of molding compound, the molding compound being partially cured prior to being fused with the first section of the attachment medium, and wherein the integral joint is formed by pressing the graphite mesh and the plate of molding compound together at an elevated temperature.

28. A prosthetic device, comprising:
a liner having a distinct shape corresponding to a limb stub of a particular patient;
a reinforcement member configured to be attached to a selected site on the liner subject to force loading, the reinforcement member having a high strength; and
an attachment medium having a first section bonded to the reinforcement member and a second section extending from the reinforcement member to cover a force distribution area of the liner substantially surrounding the selected site, the second section of the attachment medium being a web comprising a carbon graphite mesh that conforms to the distinct shape of the liner at the force distribution area to define an anchor stratum in the prosthetic device, and the second section being bonded to the liner, wherein the bond between the carbon graphite mesh and the reinforcement member comprises a fused section in which a portion of the carbon graphite mesh and a portion of the reinforcement member form an integral joint.

29. The universal reinforcement assembly of claim 28 wherein the reinforcement member comprises a plate of molding compound, the molding compound being partially cured prior to being fused with the carbon graphite mesh.

30. A reinforcement assembly in a laminated structure of a prosthetic device, comprising:
a reinforcement member configured to be attached to a selected site on a body subject to force loading, the reinforcement member having a high strength;
an attachment medium including a compliant mesh of woven strands adapted to conform to a contour of the body prior to lamination, the attachment medium having a first section and a second section extending from the first section; and
a fused joint attaching the first section of the attachment medium to a perimeter portion of the reinforcement member, the fused joint being a section in which a portion of the perimeter of the reinforcement member is merged with the mesh.

* * * * *